United States Patent [19]

Mikulicz et al.

[11] 3,993,706

[45] Nov. 23, 1976

[54] ACID PURIFICATION AND RECYCLE IN HF-CATALYZED ALKYLATION

[75] Inventors: Michael Z. Mikulicz, Palatine; Vance P. Burton, Arlington Heights, both of Ill.

[73] Assignee: UOP Inc., Des Plaines,, Ill.

[22] Filed: Oct. 28, 1975

[21] Appl. No.: 626,529

[52] U.S. Cl. .......................................... 260/683.48
[51] Int. Cl.[2] .......................................... C07C 3/54
[58] Field of Search .............................. 260/683.48

[56] References Cited
UNITED STATES PATENTS

| | | | |
|---|---|---|---|
| 2,322,800 | 6/1943 | Frey | 260/683.48 |
| 2,394,906 | 2/1946 | Frey | 260/683.48 |
| 3,594,444 | 7/1971 | Jones | 260/683.48 |
| 3,755,492 | 8/1973 | Anderson | 260/683.48 |
| 3,919,342 | 11/1975 | Chapman | 260/683.48 |

Primary Examiner—George Crasanakis
Attorney, Agent, or Firm—James R. Hoatson, Jr.; Robert W. Erickson; William H. Page, II

[57] ABSTRACT

An improved HF alkylation process for producing alkylated isoparaffins wherein capital cost, operating costs and energy consumption are reduced by elimination of the necessity of the commonly-included catalyst regeneration facilities. Hydrocarbonaceous polymers which form collateral to alkylation reactions occurring in a reaction zone, and which contaminate the acid catalyst therein, are routed to pass through reboiling means of two fractionators whereby HF and some combined fluorides in the polymers are removed and the polymers exit the process with an alkylate product. Some decomposition of the combined fluorides prevents fluorine contamination of the alkylate product.

7 Claims, 1 Drawing Figure

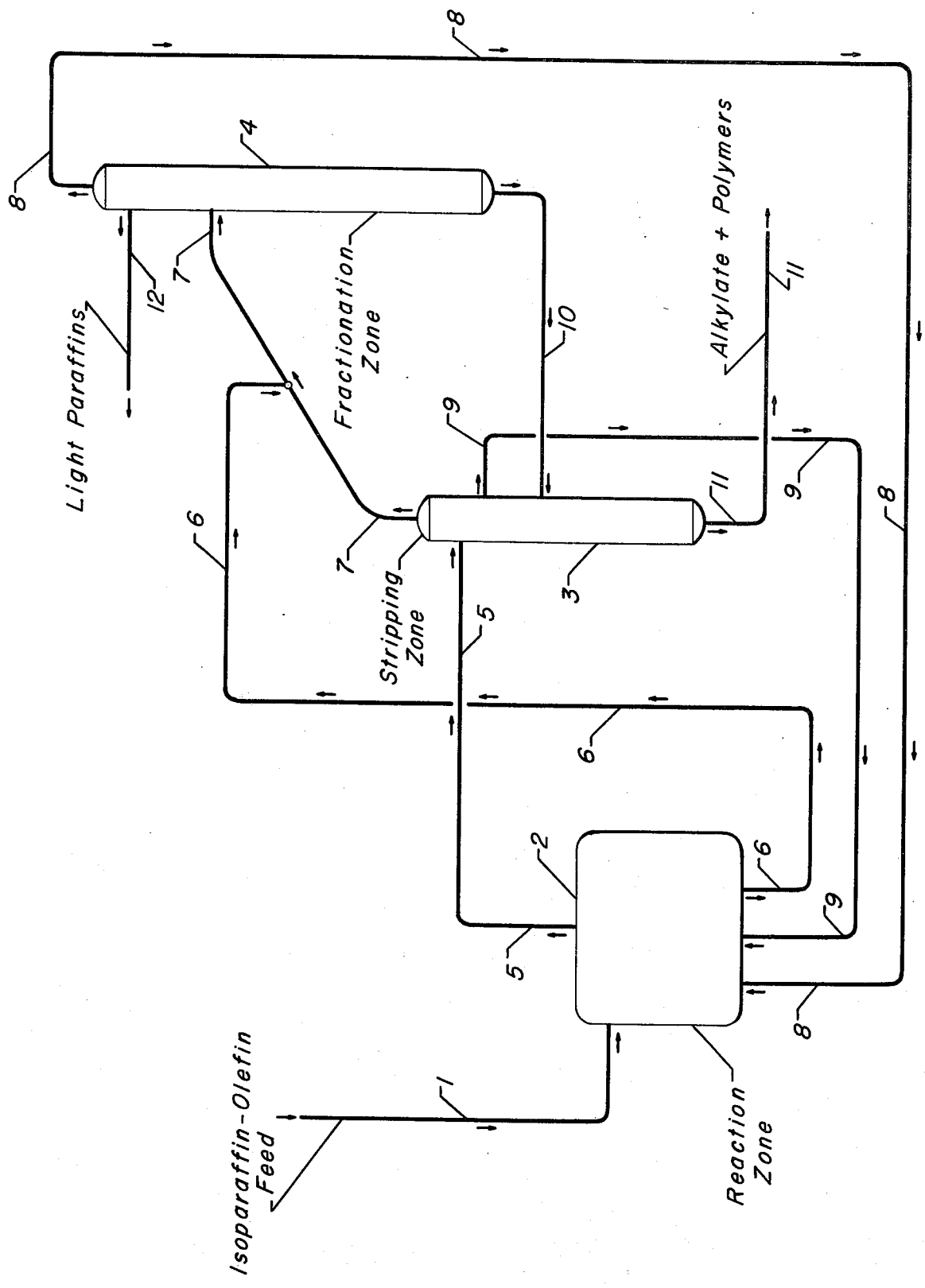

ACID PURIFICATION AND RECYCLE IN HF-CATALYZED ALKYLATION

BACKGROUND OF THE INVENTION

1. Field of the Invention

The field of art to which this invention pertains is hydrocarbon processing. It particularly relates to an improved process for the alkylation of isoparaffins with olefins.

2. Prior Art

The production of higher molecular weight isoparaffins, having valuable antiknock properties as motor fuel is of considerable importance in the petroleum refining industry. This is particularly true in recent times due to the progressive restrictions which are being placed upon the use of leadcontaining octane-improving agents. A convenient source of such higher molecular weight isoparaffins is the hydrogen fluoride-catalyzed alkylation of lower boiling isoparaffinic hydrocarbons, such as isobutane, with olefinic hydrocarbons, such as propene and butenes.

It is essential, for commercial process acceptablility, that HF catalyst utilized in alkylation processes exhibit a prolonged capability for performing its intended function as well as a high degree of activity in effecting such function. Catalyst regenerating equipment is commonly provided in HF alkylation units to periodically remove contaminants, such as hydrocarbonaceous polymers, from the catalyst in order to maintain activity. Polymers are byproducts in the alkylation process, and certain of the polymer species which are continually formed tend to remain within the catalyst. The catalyst regeneration facilities generally used represent a large capital investment in installation, maintenance and operation. It is common to regenerate HF catalyst by distilling or vapor stripping in equipment dedicated solely to this purpose. Such facilities commonly include a multistage stripping or distillation tower with its associated heating and condensing apparatuses, pumps, valves, etc.

Our invention presents a novel and emminently useful improvement over the prior art in providing an HF catalyzed alkylation process in which no regeneration facilities, per se, are required.

BRIEF SUMMARY OF THE INVENTION

Our invention involves an improved process for producing alkylate products wherein HF alkylation catalyst is utilized and its content in contaminating hydrocarbonaceous polymers is maintained at low, acceptable levels without the use of an acid regenerator. HF alkylation catalyst containing hydrocarbonaceous polymers is withdrawn from a reaction zone and passed to a fractionation zone where HF is recovered essentially free from hydrocarbonaceous polymers. The purified HF is returned to the reaction zone. The polymers traverse reboiling means in the fractionation zone where partial decomposition of combined fluorine compounds takes place. The polymers then pass to a stripping zone and therein traverse a second reboiling means where some further defluorination of the polymers occurs. The polymers then exit the stripping zone in an alkylate product.

OBJECTS AND EMBODIMENTS

A principal object of the present invention is to effect an improvement in the hydrogen fluoride alkylation of hydrocarbons. Another objective is to reduce the cost of a process for the alkylation of an isoparaffin with an olefinic hydrocarbon to produce an alkylate product.

Yet another object of our invention involves the elimination of the acid regenerator in a hydrogen fluoride alkylation process for the production of alkylated isoparaffins.

In one embodiment, our inventive concept encompasses a process for the HF-catalyzed alkylation of an isoparaffin with an olefin to produce an alkylate product, which process comprises the steps of: (i) reacting said isoparaffin with said olefin, in the presence of a hydrogen fluoride alkylation catalyst comprising hydrogen fluoride and hydrocarbonaceous polymers, in a reaction zone; (ii) withdrawing from said reaction zone a hydrocarbon phase comprising hydrogen fluoride, light paraffins, alkylate product and unreacted isoparaffins, and sending said hydrocarbon phase to a stripping zone operated at conditions selected to provide a first stream comprising alkylate product and polymer products, a second stream comprising unreacted isoparaffins and a third stream comprising hydrogen fluoride and light paraffins; (iii) passing said third stream comprising hydrogen fluoride and light paraffins to a fractionation zone operated at conditions selected to provide a fourth stream comprising polymer products, a fifth stream comprising light paraffins and a sixth stream comprising hydrogen fluoride substantially free from hydrocarbonaceous polymers; (iv) passing said fourth stream comprising polymer products from said fractionation zone to said stripping zone; (v) withdrawing a portion of said hydrogen fluoride alkylation catalyst from said reaction zone and introducing said portion into admixture with said third stream prior to the introduction of said third stream into said fractionation zone, said portion of said hydrogen fluoride alkylation catalyst being sufficient to completely dissolve within said third stream to form a homogeneous mixture free from a separate hydrogen fluoride phase; and, (vi) introducing said sixth stream comprising hydrogen fluoride substantially free from hydrocarbonaceous polymers into said reaction zone.

BRIEF DESCRIPTION OF THE DRAWING

The attached drawing illustrates a particular embodiment of the present invention. Only such details are included as are necessary for a clear understanding of our invention, and no intention is thereby made to unduly limit its scope. Certain items necessary to the operation of the process of this invention but unnecessary to its understanding, such as certain process streams, valves, pumps, instrumentation and other equipment, have been omitted for the sake of clarity.

The drawing is a schematic representation of a hydrogen fluoride alkylation process for the production of alkylate from isoparaffins and olefins. An alkylation feed stream, or streams, containing olefins, isoparaffins and light paraffins enters reaction zone 2 in conduit 1 and contacts hydrogen fluoride catalyst therein. A resulting mixture, comprising alkylate, unreacted isoparaffins, hydrogen fluoride and light paraffins exits the reaction zone in conduit 5, passing to stripping zone 3. Unreacted isoparaffins from the hydrocarbon mixture exit stripping zone 3 in conduit 9 and pass to reaction zone 2 to further participate in the reactions taking place therein. Light paraffins and hydrogen fluoride exit the stripping zone in conduit 7. Hydrogen fluoride catalyst, containing hydrocarbonaceous polymers, exits reaction zone 2 in conduit 6 and passes to conduit 7, intimately mixing with and dissolving into light paraffins therein from stripping zone 3. The admixture of light paraffins, hydrogen fluoride and hydrocarbonaceous polymers in conduit 7 then proceeds to fractionation zone 4. Hydrogen fluoride, essentially free from hydrocarbonaceous polymers exits the fractionation zone in conduit 8 and returns to reaction zone 2. Light paraffins exit the fractionation zone in conduit 12. hydrocarbonaceous polymers exit the fractionation zone in conduit 10 and pass to stripping zone 3. An alkylate product, containing hydrocarbonaceous polymers exits stripping zone 3 in conduit 11.

DETAILED DESCRIPTION OF THE INVENTION

Our invention is directed toward an improved process for alkylating isoparaffins with olefins.

This improved process is particularly applicable to the alkylation of isobutane with a butylene-containing olefinic stream for the production of motor fuel alkylates, however, it is also adaptable for use with other isoparaffins and olefins. Suitable isoparaffins have from about 4 to about 7 carbon atoms per molecule, including isobutane, isopentane, neopentane, isohexanes and heptanes having branched chains. Suitable olefins have from about 3 to about 7 carbon atoms per molecule and include propylene, 1-butene, 2-butene, isobutylene, amylenes, hexenes and heptenes and mixtures of these compounds. The HF alkylation catalysts suitable for use include catalysts in which hydrogen fluoride is the principal active ingredient. These catalysts are most beneficial if they contain about 90 weight percent HF and less than 10 weight percent water. The most advantageous catalyst is one having about 88 weight percent HF, less than 2 weight percent water and the balance of 100 weight percent as soluble organic compounds, sometimes referred to as organic diluent. The most suitable organic diluent is that which results from operation of HF within our alkylation process. That is to say, placement of a catalyst comprising 98–100 weight percent HF into our process will, after a short operational period, acquire the required organic diluent. We prefer to use this method to acquire the organic diluent for any particular operation because it is believed that the most favorable diluent is one which is formed from precursors existing in the feed to the particular operation in question.

Reactants in the isoparaffin alkylation process of our invention combine to yield as principal products alkylated hydrocarbons, or alkylate products, of carbon content equal to the sum of the carbon atoms of the individual olefin and isoparaffin reactants which combine. This monosubstituted alkylate is most desirable because of its exceptional octane and boiling point characteristics as compared to alkylate of higher molecular weight. It is necessary, for the optimum production of primarily mono-substituted alkylate, that reaction zone conditions be maintained to favor alkylation rather than polymerization and other undesirable reactions. Of primary consideration in this regard is the maintenance of the HF catalyst in the aforementioned state of concentration and purity. As is well known in the art, olefins are exceptionally unstable compounds and have a great propensity for polymerization to form high molecular weight hydrocarbonaceous polymers. Although every attempt is made to eliminate polymerization reactions in favor of alkylation reactions in an alkylation reaction zone, it is unavoidable that some polymerization takes place. Since the polymerization is continual it is necessary to continually remove polymers in order to prevent their accumulation to unacceptable levels within the HF catalyst. If the polymer content of HF catalyst exceeds certain levels, dependent upon the particular operation, the catalytic function is impaired. This impairment can manifest itself as increased polymerization, lower alkylate quality, lower yield, and other diverse bad effects.

The harmful accumulation of hydrocarbonaceous polymers is avoided in the alkylation process of our invention. The essence of our invention is a unique present geometry of flow which removes hydrocarbonaceous polymers from the HF catalyst and allows the polymers to escape the process with the alkylate product. Detailed explanation of our invention is most facilly accomplished with reference to the attached drawing.

In the embodiment of the process of our invention shown in the drawing isoparaffin and olefin reactants contact HF alkylation catalyst in a reaction zone. Note that it is often impractical to acquire a feed which is composed exclusively of the desired isoparaffin and olefin components. For this reason the feed ordinarily contains some constitutents which pass through the process without entering into reactions therein. As an example, when isobutane is being alkylated with propylene, the feed will commonly contain some paraffins such as propane and butane. Such materials will be referred to in these teachings as light paraffins. Thorough admixture and settling of the hydrocarbon and acid materials take place within the reaction zone so that a hydrocarbon phase separates from an HF phase, the hydrocarbon phase comprising alkylate, unreacted isoparaffins, light paraffins and dissolved HF. The reaction zone may be any of the well known prior art devices for effecting alkylation reactions, such as a vertical or horizontal contact vessel for bringing the reactants and catalyst into intimate contact in a state of dispersion, subsequent mixing facilities for the continuation of reactions to completion, and subsequent settling facilities for separation of the hydrocarbons from the catalyst. The hydrocarbons, now collected into a hydrocarbon phase, are withdrawn from the reaction zone and passed to a stripping zone where alkylate is separated from hydrogen fluoride and unreacted isoparaffins. Unreacted isoparaffins are returned to the reaction zone for participation in the alkylation reactions taking place there.

The stripping zone may be any of the well known apparatuses for stripping, such as vertically oriented, multistage plate or packed towers, fed at the top and provided with reboiling means at the bottom. The conditions of operation of the stripping zone depend upon the particular hydrocarbon feed constituents being used, however, they should be chosen to provide a bottoms product from the stripping zone substantially free from HF, light paraffins or unreacted isoparaffins.

The aforesaid HF phase in the reaction zone has acquired hydrocarbonaceous polymers, or polymer products, through contact with the feed. In order to remove hydrocarbonaceous polymers in a unique and very economical way we preset the geometry of process flow as follows. A small portion of the HF phase is withdrawn from the reaction zone and is dissolved within the HF + light paraffins stream previously withdrawn from the stripping zone. It is essential to the optimum utility of our invention that the portion of HF phase be chosen in quantity less than or equal to the amount which will fully dissolve within the HF + light paraffin stream before entering the aforementioned fractionation zone. This is necessary to avoid introduction of a free liquid HF phase into the fractionation zone. It is preferable not to introduce an HF phase into the fractionation zone. HF in solution in a liquid hydrocarbon phase is much less corrosive and much less prone to precipitation of troublesome solid deposits than HF in a liquid HF phase, and less sophisticated materials of construction and simpler maintenance techniques therefore result from avoidance of the existence of a liquid HF phase in the feed to the fractionation zone. It is preferred to adjust the rate of injection of HF phase into the fractionation zone feed based upon solubilitytemperature relations well known to those skilled in the art. It is common practice in the art to preheat the feed to a fractionation zone before its introduction thereto. In raising the temperature of the HF + light paraffin stream from the stripping zone, prior to its introduction into the fractionation zone, the solubility of HF in the HF + light paraffin stream in increased. We introduce HF catalyst into the stream after preheating and thereby take advantage of the ability of the fractionation zone feed to dissolve HF in addition to the HF already dissolved therein. In a particular unit corresponding to the embodiment shown in the attached drawing the temperature of the fractionation zone feed was 160° F after preheating, and we set the injection not to exceed 2.7 weight percent HF in the fractionation zone feed in order to assure complete dissolution of HF therein.

Our experience is that a quantity of HF phase, or HF catalyst, from the reaction zone equivalent to or slightly less than the limit of solubility of HF in the HF + light paraffin stream from the stripping zone is more than sufficient to maintain the content of polymer products in the HF catalyst at acceptable levels in the reaction zone.

The homogeneous solution of HF, polymer products and light paraffins is now passed to the aforementioned fractionation zone where it is separated into a light paraffin stream, a purified HF stream, substantially reduced in polymer content, and a polymer stream. The purified HF stream is returned to the reaction zone for further catalytic use. The fractionation zone may be any one of the common fractionating apparatuses in use, such as a vertically disposed plate or packed tower having a feed inlet at a central section, reboiling means in a bottom section and provision for reflux to a top section. The conditions of operation depend upon the boiling point and vapor pressure characteristics of the particular materials involved. These conditions should be chosen to provide a bottoms polymer stream substantially free from light paraffins and a light paraffin stream substantially free from polymer products. Selection of these operating conditions is based upon well known principles of fractionation and is well within the abilities of those skilled in the art. Polymers within the fractionation zone pass downwardly and exit the fractionation zone as a polymer stream after having traversed a reboiling means. The polymer stream is returned to the stripping zone, and the polymers therein contained exit the stripping zone in the alkylate stream after having traversed the reboiling means in the stripping zone.

By the unique flow path of the process of our invention we maintain the purity of the HF catalyst within optimum limits without the provision of prior art devices for catalyst regeneration. Another facet of particular novelty in our invention is that the polymer products are routed through the process in such a way that they must traverse two reboiling means before exiting. The utility of this feature is concerned with the decomposition of fluorine compounds which are invariably present within the polymer products. Polymers with combined fluorine are converted to HF and polymers by high temperatures encountered in the two aforementioned reboiling means. Fluorine does not, therefore, substantially contaminate the alkylate, as would be the case if polymers within the alkylate contained combined HF. Passage through two reboilers assures substantial fluorine removal. The following characteristics are representative of alkylate produced in the embodiment of our invention shown in the attached drawing. Shown are laboratory analyses and corresponding results.

| ANALYSIS | RESULT |
|---|---|
| Copper strip corrosion 122° F — 3 hrs. | 1A |
| ASTM gum, mg/100 ml | 1 |
| Fluoride, wt-ppm | 25 |
| Saybolt color | +20 |
| A.P.I. Gravity at 60° F | 72.9 |
| Specific Gravity at 60° F | 0.6923 |
| Distillation ASTM D86 | |
| IBP ° F | 100 |
| 5 | 133 |
| 10/20 | 154/185 |
| 30/40 | 200/206 |
| 50/60 | 210/216 |
| 70/80 | 222/232 |
| 90/95 | 278/370 |
| EP | 389 |
| % Recovered | 96.5 |
| % Bottoms | 1.5 |
| % Loss | 2.0 |
| Octane Rating | |
| Research clear | 93.3 |
| Research + 3 CCTEL | 104.7 |
| CCTEL/gal of isooctane equiv. | 0.43 |
| Motor clear | 91.7 |
| COMPOSITION WT-%, BY GAS CHROMATOGRAPHY | |
| $C_4$ Components | |
| Isobutane | 0.1 |
| n-Butane | 7.0 |
| $C_5$ Components | |
| Isopentane | 6.0 |
| n-Pentane | 0.2 |
| $C_6$ Components | |
| 2,3-dimethylbutane | 1.6 |
| 2-methylpentane | 0.5 |
| 3-methylpentane | 0.2 |
| $C_7$ Components | |
| 2,4-dimethylpentane | 7.2 |
| 2,2,3-trimethylbutane | to |
| 2-methylhexane | 0.2 |
| 2,3-dimethylpentane | 15.7 |
| 3-methylhexane | 0.2 |
| $C_8$ Components | |
| 2,2,4-trimethylpentane | 31.8 |
| 2,5-dimethylhexane | 1.4 |
| 2,4-dimethylhexane | 2.4 |
| 2,2,3-trimethylpentane | 0.7 |
| 2,3,4-trimethylpentane | 8.2 |
| 2,3,3-trimethylpentane | 6.0 |
| 2,3-dimethylhexane & 2-methyl-3-ethylpentane | 2.4 |
| 4-methylheptane & 3,4-dimethylhexane | 0.3 |
| 3-methylheptane | 92.1 |
| HEAVIER COMPONENTS BY BOILING RANGE | |
| $C_9$ | 0.6 |
| $C_{10}$ | 2.8 |
| $C_{11}$ | 2.6 |
| $C_{12}$ | 1.4 |
| $C_{13}+$ | 0.5 |

U.S. Pat. No. 2,372,338 (Mar. 27, 1945) discloses a process for HF alkylation wherein the HF catalyst is purified in the same process step in which alkylate is recovered. It should be noted that in that process the polymer products only must traverse one reboiling means whereas our invention provides an improved flow path involving two reboiling means for improved decomposition of combined fluorides in the polymer products. Our invention involves introduction of HF catalyst not into the product separation zone but into a downstream zone. Our invention is further distinguished from and further improves upon the prior art in that provision of an extra heater for the HF catalyst prior to introduction into a fractionation zone would be unnecessary and undesirable in our process, whereas it may be required in the prior art process. Other distinguishing features will become apparent from perusal of the prior art reference.

Reasonable variation and modification are possible within the scope of the foregoing disclosure, the drawing and the claims to the invention without departing from the spirit thereof.

We claim as our invention:

1. A process for the HF-catalyzed alkylation of an isoparaffin with an olefin to produce an alkylate product, which process comprises the steps of:
   i. reacting said isoparaffin with said olefin, in the presence of a hydrogen fluoride alkylation catalyst comprising hydrogen fluoride containing hydrocarbonaceous polymers, in a reaction zone;
   ii. separating a hydrocarbon phase and a catalyst phase from step (i);
   iii. passing said hydrocarbon phase to a stripping zone operated at conditions selected to withdraw a first stream comprising alkylate product including said hydrocarbonaceous polymers, a second stream comprising unreacted isoparaffins and a third stream comprising hydrogen fluoride and light paraffins;
   iv. passing said third stream comprising hydrogen fluoride and light paraffins and a portion of said catalyst phase, as hereinafter delineated to a fractionation zone operated at conditions selected to provide a fourth stream comprising said hydrocarbonaceous polymers, a fifth stream comprising light paraffins and a sixth stream comprising hydrogen fluoride substantially free from said hydrocarbonaceous polymers;
   v. passing said fourth stream comprising said hydrocarbonaceous polymers from said fractionation zone to said stripping zone;
   vi. said portion of said hydrogen fluoride alkylation catalyst phase being admixed with said third stream in step (iv) being sufficient to completely dissolve within said third stream to form a homogeneous mixture free from a separate hydrogen fluoride phase; and,
   vii. introducing said sixth stream comprising hydrogen fluoride substantially free from hydrocarbonaceous polymers into said reaction zone.

2. The process of claim 1 further characterized in that said isoparaffin contains from about 4 to about 7 carbon atoms per molecule.

3. The process of claim 1 further characterized in that said olefin contains from about 3 to about 7 carbon atoms per molecule.

4. The process of claim 1 further characterized in that said isoparaffin is isobutane.

5. The process of claim 1 further characterized in that said olefin is propylene.

6. The process of claim 1 further characterized in that said olefin is a butylene.

7. The process of claim 1 further characterized in that said olefin is a mixture of propylene and butylene.

* * * * *